United States Patent [19]

Malpass et al.

[11] Patent Number: 4,910,178

[45] Date of Patent: Mar. 20, 1990

[54] OLEFIN POLYMERIZATION OR COPOLYMERIZATION CATALYST COMPONENTS

[75] Inventors: Dennis B. Malpass, LaPorte, Tex.; Michael J. Breen, Erie, Pa.; Loyd W. Fannin, Dickinson, Tex.

[73] Assignee: Texas Alkyls, Inc., Deer Park, Tex.

[21] Appl. No.: 251,278

[22] Filed: Sep. 30, 1988

[51] Int. Cl.$^4$ ............................................. C08F 4/64
[52] U.S. Cl. .................................. 502/103; 502/108; 502/118; 556/190
[58] Field of Search ................. 502/103, 108, 118; 556/190

[56] References Cited

U.S. PATENT DOCUMENTS 3,256,253  6/1966  Neumann et al. ................. 260/80
4,311,816  1/1982  Mollison et al. ................ 502/115 X Primary Examiner—Patrick P. Garvin
Attorney, Agent, or Firm—Richard P. Fennelly; Louis A. Morris

[57] ABSTRACT

Adducts of a trialkylaluminum or a dialkylaluminum hydride and diisoalkenyl benzene compounds have been discovered. Catalyst components for the polymerization of olefins have also been developed which comprise, as the cocatalyst, the reaction product of a trialkylaluminum or a dialkylaluminum hydride (e.g., diisobutylaluminum hydride) and an alkenyl-substituted benzene (e.g., diisopropenyl benzene).

6 Claims, No Drawings

OLEFIN POLYMERIZATION OR COPOLYMERIZATION CATALYST COMPONENTS

BACKGROUND OF THE PRESENT INVENTION

1. Field of the Invention

The present invention pertains to catalyst components for the polymerization of olefins. The catalyst components contain an aluminum-containing cocatalyst composition prepared by reaction of a trialkylaluminum or a dialkylaluminum hydride with an alkenyl-substituted benzene compound.

2. Description of the Prior Art

U.S. Pat. No. 3,256,253 shows (in Example 7) the reaction between p-divinyl benzene and diisobutyl aluminum hydride in the formation of organic tin compounds.

SUMMARY OF THE PRESENT INVENTION

The present invention relates to certain novel adducts and to their use as cocatalyst components in olefin polymerization reactions. For example, the adduct formed by reaction of a dialkylaluminum hydride and a diisoalkenyl benzene is believed to be novel. The catalyst components containing the reaction product of a dialkylaluminum hydride with an alkenyl-substituted benzene compound are also deemed novel.

DETAILED DESCRIPTION OF THE PRESENT INVENTION

The novel adducts of the present invention comprise the reaction product of: (1) a trialkylaluminum or a dialkylaluminum hydride; and (2) a diisoalkenyl benzene compound. The trialkylaluminum or dialkylaluminum hydrides have the formulae $R_3Al$ or $R_2AlH$ where R is an alkyl group of from about 2 to about 8 carbon atoms in length. Both straight and branched chain alkyl groups are contemplated, however, branching at the second carbon is preferred for facile olefin elimination. A very preferred alkyl group is isobutyl. The diisoalkenyl benzene compounds consist of an aryl ring containing two isoalkenyl groups, e.g., those with from about 3 to about 6 carbon atoms each. Preferred as an isoalkenyl group is isopropenyl. These reaction products are prepared by reacting the trialkylaluminum or dialkylaluminum hydride and the diisoalkenyl benzene compound at mole ratios of about 1:1 to about 2:1 at temperatures of 75° C. to about 140° C. with removal of evolved olefin. The reaction can be carried out without solvent. The evolved olefin corresponds to the alkyl groups in the trialkylaluminum or dialkylaluminum hydride.

The adducts formed are useful as aluminum-containing cocatalyst components with conventionally known Ziegler-Natta olefin polymerization catalysts. Examples of such catalysts include the titanium-containing, magnesium chloride-supported catalyst components known to persons of ordinary skill in the art. A representative example of such a catalyst is described in U.S. Pat. No. 4,359,561 although others which are known to the art may also be used.

The foregoing invention is further illustrated by the Examples which follow.

EXAMPLE 1

A 500-milliliter round-bottom flask fitted with a dropping funnel, condenser (refrigerated oil), thermometer and rubber septum inlet port was charged with 73.6 grams (0.518 mole) of diisobutylaluminum hydride (DIBAL-H) under a nitrogen atmosphere. Contents of the flask were heated to 115° C. in an oil bath which was heated by a hot plate-stirrer. Forty-five milliliters (41.0 grams, 0.259 mole) of m-diisopropenyl benzene was added from the dropping funnel over a 25 minute period. A slow purge of nitrogen was passed through the flask during the reaction to remove isobutylene. After heating three hours in the range of 115°-127° C., about 11 milliliters of isobutylene was collected in a dry ice-alcohol trap. At this stage, the hot reaction product was clear, colorless and not viscous. When cooled to ambient temperature for sampling, however, the product was too viscous to allow stirring by the magnetic stir bar.

The reaction was continued at 135°-140° C. for three more hours under a nitrogen purge. After an additional 6 milliliters was collected in the trap, no more isobutylene was evolved. Upon cooling to ambient temperature, the product (coded "DA-1") was a clear, colorless liquid having the viscosity of honey. Analyses of the product are given in the attached Table.

EXAMPLE 2

A flask as described in Example 1 was charged with 64.2 grams (0.406 mole) of solid p-diisopropenyl benzene under an atmosphere of nitrogen. Diisobutylaluminum hydride (116.3 grams, 0.818 mole) was added from the dropping funnel to the melted solid at 75°-85° C. over about an hour's time. Nitrogen purging was not used in this Example and lower temperatures were used to minimize displacement of isobutylene. After heating for an additional three hours at about 85° C., the reaction flask was cooled to ambient temperature for sampling (DA-5). Removal of reaction product showed 99.4% material balance at this stage indicating essentially no loss of isobutylene.

The material was recharged to the flask and heating was continued at about 100° C. for four hours. Temperature was lowered to ambient again and another sample (DA-5A) was taken.

After continuing the reaction for an additional eight hours at about 100° C., the temperature was lowered to ambient for removal and weighing of the product. Recovered material indicated that total isobutylene loss was about 7.5 grams. The final product (coded "DA-5B") was a clear, colorless liquid of low viscosity. Analyses are given in the attached Table.

EXAMPLE 3

This reaction was conducted in a glass pressure bottle fitted with a pressure gauge, thermowell, diptube and magnetic stirring bar. Heating and stirring were supplied by a hot plate-stirrer and oil bath. Both reactants, 77.3 grams (0.543 mole) of DIBAL-H and 89.5 grams (0.566 mole) of p-diisopropenyl benzene, were charged to the pressure bottle under an atmosphere of nitrogen. Reaction was allowed to proceed at about 95° C. for eight hours during which time the pressure slowly increased to 25 psig without allowing any venting. The reactor was cooled and sampled (coded "DA-11").

The reaction was continued for another seven hours at 95° C. with venting being required several times to keep the pressure below 25 psig. The reactor was cooled and another sample (coded "DA-11A") was taken.

Final heating was at 105° C. for an additional seven hours during which time venting was required several times. The material balance indicated that about 17 grams of isobutylene were vented during the reaction. The final product (coded "DA-11B") was a clear, colorless liquid having a relatively low viscosity similar to mineral oil. Analyses of the various samples and final product are given in the attached Table.

PRODUCT ANALYSIS

| Product Code | Al Wt % | Mole % $H_2$ in Hydrolysis Gas | % Diisopropenyl Benzene | % Isopropyl-Isopropenyl Benzene | % Diisopropyl Benzene |
|---|---|---|---|---|---|
| DA-1 | 13.82 | 29.9 | 2.0 | 5.1 | 92.9 |
| DA-5 | 12.01 | 10.6 | 13.3 | 32.1 | 54.6 |
| DA-5A | 12.17 | 4.9 | 1.5 | 10.4 | 88.1 |
| DA-5B | 12.25 | 4.3 | 1.2 | 7.1 | 91.7 |
| DA-11 | 8.83 | 0.6 | 16.4 | 43.5 | 40.1 |
| DA-11A | 9.13 | 0.7 | 10.5 | 39.4 | 50.1 |
| DA-11B | 9.79 | 1.9 | 4.5 | 30.3 | 65.2 |

EXAMPLES 4–11

Slurry polymerization of ethylene in a hexane solvent employing an $SiO_2$-supported titanium catalyst component A prepared according to U.S. Pat. No. 4,359,561 (Example 1A) was conducted. The catalyst component contained 1.25% Ti. It was employed in Examples 4–7.

A second catalyst component B, was prepared in a similar procedure containing 1.05% Ti. It was employed in Examples 8–11.

A 4 liter reactor containing 2 liters of hexane was used. The stirring was at 1,000 rpm to carry out polymerizations for 60 minutes at 85° C.±1° C. (unless otherwise noted) with the reagents being added in the following order: cocatalyst; 200 mg catalyst component A or B; 40 psig hydrogen; and ethylene maintained at 150 psig. After 60 or 90 minutes, the reactor was vented, the product was filtered and was vacuum dried.

In the tables below, the following abbreviations have been used:

Al/Ti: molar ratio—aluminum: titanium
dens: bulk density
MI: melt index [ASTM method D-1238, Condition E at 190° C. 2160 gram load (expressed as grams per 10 minutes)]
MIR: melt index ratio [expressed as the ratio of the high load melt index (HLMI) to the melt index. HLMI obtained under same conditions as MI except with 21,600 gram/load, Condition F]
TIBAL: triisobutylaluminum In accordance with the usual practice, the specific activity of the catalyst is expressed as $$\text{kg polymer} \cdot \text{g Ti}^{-2} \cdot \text{atm } C_2H_4^{-1} \cdot \text{hr}^{-1}$$

The results are:

| Example No. | Cocatalyst | Al/Ti | Spec. Act. | Bulk Den. | MI | MIR |
|---|---|---|---|---|---|---|
| 4* | TIBAL** | 100 | 9.9 | 0.28 | 1.0 | 34 |
| 5* | Isoprenylaluminum | 95 | 5.3 | 0.34 | 0.4 | 34 |
| 6 | Da-1 | 83 | 7.7 | 0.28 | 0.9 | 34 |
| 7*** | DA-11B | 79 | 6.4 | 0.31 | 1.1 | 34 |
| 8* | TIBAL** | 122 | 17.9 | 0.31 | 0.8 | 27 |
| 9* | Isoprenylaluminum | 133 | 6.9 | — | 0.1 | 40 |
| 10* | Isoprenylaluminum | 103 | 5.2 | 0.32 | 0.5 | 26 |
| 11 | DA-5B | 170 | 12.4 | 0.31 | + | + |

*control
**triisobutylaluminum
***reaction time was 90 minutes.
+ temperature exceeded 90° C., MI and MIR data unreliable.

The foregoing Examples should not be construed in a limiting sense since they are intended to merely illustrate certain embodiments of the present invention. The claims which follow illustrate the scope of protection desired.

We claim:

1. A Ziegler-Natta catalyst composition for the polymerization of olefins which comprises a supported catalyst component and, as a cocatalyst, the reaction product of a dialkylaluminum hydride and an alkenyl-substituted benzene compound.

2. A Ziegler-Natta catalyst composition for the polymerization of olefins which comprises a supported catalyst component and, as a cocatalyst, the reaction product of a trialkylaluminum or a dialkylaluminum hydride and a diisoalkenyl benzene compound.

3. The catalyst composition of claim 2 wherein the hydride contains two $C_2$–$C_8$ alkyl groups.

4. The catalyst composition of claim 2 wherein the hydride is diisobutylaluminum hydride.

5. The catalyst composition of claim 2 wherein the diisoalkenyl benzene is diisopropenyl benzene.

6. The catalyst composition of claim 4 wherein the diisoalkenyl benzene is diisopropenyl benzene.

* * * * *